United States Patent
Somberg et al.

(10) Patent No.: US 12,403,109 B2
(45) Date of Patent: **\*Sep. 2, 2025**

(54) SOTALOL HYDROCHLORIDE DOSING

(71) Applicant: AltaThera Pharmaceuticals LLC, Chicago, IL (US)

(72) Inventors: John Somberg, Chicago, IL (US); Brandon Ira Kashfian, Chicago, IL (US); Janos Molnar, Chicago, IL (US)

(73) Assignee: AltaThera Pharmaceuticals LLC, Chicago, IL (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/725,189

(22) Filed: Apr. 20, 2022

(65) Prior Publication Data
US 2022/0241225 A1    Aug. 4, 2022

Related U.S. Application Data

(63) Continuation of application No. 16/946,941, filed on Jul. 13, 2020, now Pat. No. 11,344,518, which is a continuation-in-part of application No. 16/863,567, filed on Apr. 30, 2020, now abandoned, and a continuation-in-part of application No. 16/693,310, filed on Nov. 24, 2019, now Pat. No. 11,696,902, which is a continuation-in-part of application No. 16/103,815, filed on Aug. 14, 2018, now Pat. No. 10,512,620, said application No. 16/863,567 is a continuation-in-part of application No. 16/693,312, filed on Nov. 24, 2019, which is a continuation of application No. 16/103,815, filed on Aug. 14, 2018, now Pat. No. 10,512,620, said application No. 16/946,941 is a continuation-in-part of application No. 16/849,099, filed on Apr. 15, 2020, now abandoned.

(60) Provisional application No. 63/009,511, filed on Apr. 14, 2020, provisional application No. 62/987,832, filed on Mar. 10, 2020.

(51) Int. Cl.
A61P 9/06     (2006.01)
A61K 9/00     (2006.01)
A61K 31/18    (2006.01)

(52) U.S. Cl.
CPC ............ *A61K 31/18* (2013.01); *A61K 9/0019* (2013.01); *A61P 9/06* (2018.01)

(58) Field of Classification Search
CPC ............ A61P 9/06; A61K 9/0019; A61K 9/20
See application file for complete search history.

(56) References Cited

U.S. PATENT DOCUMENTS

| | | |
|---|---|---|
| 6,043,273 A | 3/2000 | Duhaylongsod |
| 6,060,454 A | 5/2000 | Duhaylongsod |
| 6,101,412 A | 8/2000 | Duhaylongsod |
| 6,124,363 A | 9/2000 | Appleby et al. |
| 6,136,327 A | 10/2000 | Gupta et al. |
| 6,281,246 B2 | 8/2001 | Sankaranarayanan |
| 6,369,114 B1 | 4/2002 | Weil et al. |
| 6,482,811 B1 | 11/2002 | Bacaner et al. |
| 6,491,039 B1 | 12/2002 | Dobak, III |
| 6,500,459 B1 | 12/2002 | Chhabra et al. |
| 6,544,981 B2 | 4/2003 | Stein et al. |
| 6,627,223 B2 | 9/2003 | Percel et al. |
| 6,632,217 B2 | 10/2003 | Harper et al. |
| 6,645,524 B2 | 11/2003 | Midha et al. |
| 6,720,001 B2 | 4/2004 | Chen et al. |
| 6,800,668 B1 | 10/2004 | Odidi et al. |
| 6,899,700 B2 | 5/2005 | Gehling et al. |
| 6,916,813 B2 | 7/2005 | Atwal et al. |
| 7,004,171 B2 | 2/2006 | Benita et al. |
| 7,005,425 B2 | 2/2006 | Belardinelli et al. |
| 7,005,436 B2 | 2/2006 | Lloyd et al. |
| 7,022,343 B2 | 4/2006 | Philbrook et al. |
| 7,048,945 B2 | 5/2006 | Percel et al. |
| 7,090,830 B2 | 8/2006 | Hale et al. |
| 7,179,597 B2 | 2/2007 | Woosley |
| 7,289,847 B1 | 10/2007 | Gill et al. |
| 7,341,737 B2 | 3/2008 | Gehling et al. |
| 7,371,254 B2 | 5/2008 | Dobak, III |
| 7,396,524 B2 | 7/2008 | Yan |
| 7,417,038 B1 | 8/2008 | Anker et al. |
| 7,526,335 B2 | 4/2009 | Ferek-Petric |
| 7,538,092 B2 | 5/2009 | Orlando et al. |
| 7,572,776 B2 | 8/2009 | Yu et al. |
| 7,674,820 B2 | 3/2010 | Fedida et al. |
| 7,745,665 B2 | 6/2010 | Gant et al. |
| 7,765,110 B1 | 7/2010 | Koneru |
| 7,776,844 B2 | 8/2010 | Yu et al. |
| 7,815,936 B2 | 10/2010 | Hasenzahl et al. |
| 7,829,573 B2 | 11/2010 | Curwen et al. |

(Continued)

FOREIGN PATENT DOCUMENTS

| | | | |
|---|---|---|---|
| AU | 737668 B2 | 8/2001 |
| AU | 765269 B2 | 9/2003 |

(Continued)

OTHER PUBLICATIONS

U.S. Appl. No. 63/009,511, filed Apr. 14, 2020, John Charin Somberg.
(Devlin, Jodi) Co-pending U.S. Appl. No. 17/566,840, filed Dec. 31, 2021, Specification, Claims, and Figures.
(Ivaturi, Vijay et al.) U.S. Appl. No. 16/376,706, filed Apr. 5, 2019, Specification, Claims, Figures.

(Continued)

*Primary Examiner* — Anna R Falkowitz
*Assistant Examiner* — John P Nguyen
(74) *Attorney, Agent, or Firm* — New River Valley IP Law, P.C.; Michele L. Mayberry; Ashley M. Gates

(57) ABSTRACT

The present invention provides novel methods of administering sotalol hydrochloride to patients in need thereof.

7 Claims, No Drawings

(56) References Cited

U.S. PATENT DOCUMENTS

| | | |
|---|---|---|
| 7,846,968 B2 | 12/2010 | Chien et al. |
| 7,885,824 B1 | 2/2011 | Koneru |
| 7,885,827 B1 | 2/2011 | Koneru |
| 7,951,183 B2 | 5/2011 | Dobak, III |
| 8,106,099 B2 | 1/2012 | Brendel et al. |
| 8,236,782 B2 | 8/2012 | Mosher et al. |
| 8,263,125 B2 | 9/2012 | Vaya et al. |
| 8,268,352 B2 | 9/2012 | Vaya et al. |
| 8,313,757 B2 | 11/2012 | Lengerich |
| 8,377,994 B2 | 2/2013 | Gray et al. |
| 8,399,018 B2 | 3/2013 | Lichter et al. |
| 8,440,168 B2 | 5/2013 | Yang et al. |
| 8,465,769 B2 | 6/2013 | Petereit et al. |
| 8,466,277 B2 | 6/2013 | Orlando et al. |
| 8,575,348 B2 | 11/2013 | Rao et al. |
| 8,696,696 B2 | 4/2014 | Solem |
| 8,709,076 B1 | 4/2014 | Matheny et al. |
| 8,753,674 B2 | 6/2014 | Helson |
| 8,828,432 B2 | 9/2014 | Lengerich |
| 8,865,213 B2 | 10/2014 | Sheth et al. |
| 8,871,452 B2 | 10/2014 | Lee |
| 8,906,847 B2 | 12/2014 | Cleemann et al. |
| 8,962,574 B2 | 2/2015 | Reilly |
| 8,987,262 B2 | 3/2015 | Eaute-Labreze et al. |
| 9,011,526 B2 | 4/2015 | Matheny |
| 9,016,221 B2 | 4/2015 | Brennan et al. |
| 9,044,319 B2 | 6/2015 | Matheny |
| 9,060,969 B2 | 6/2015 | Matheny |
| 9,078,929 B2 | 7/2015 | Kuebelbeck et al. |
| 9,161,952 B2 | 10/2015 | Matheny et al. |
| 9,239,333 B2 | 1/2016 | Snider |
| 9,255,104 B2 | 2/2016 | Rao et al. |
| 9,308,084 B2 | 4/2016 | Matheny |
| 9,399,067 B2 | 7/2016 | Mosher et al. |
| 9,474,719 B2 | 10/2016 | Mullen et al. |
| 9,498,481 B2 | 11/2016 | Rao et al. |
| 9,549,912 B2 | 1/2017 | Milner et al. |
| 9,554,989 B2 | 1/2017 | Kaplan et al. |
| 9,585,851 B2 | 3/2017 | Yun et al. |
| 9,585,884 B2 | 3/2017 | Rao et al. |
| 9,597,302 B1 | 3/2017 | Yan et al. |
| 9,616,026 B2 | 4/2017 | Singh |
| 9,682,041 B2 | 6/2017 | Helson |
| 9,724,297 B2 | 8/2017 | Thomas et al. |
| 9,770,514 B2 | 9/2017 | Ghebre-Sellassie et al. |
| 9,889,148 B2 | 2/2018 | Daemmgen et al. |
| 9,995,756 B2 | 6/2018 | Saffitz et al. |
| 10,117,881 B2 | 11/2018 | Helson |
| 10,238,602 B2 | 3/2019 | Helson et al. |
| 10,258,691 B2 | 4/2019 | Helson et al. |
| 10,349,884 B2 | 7/2019 | Helson et al. |
| 10,357,458 B2 | 7/2019 | Helson |
| 10,449,193 B2 | 10/2019 | Helson et al. |
| 10,450,267 B2 | 10/2019 | Stancl |
| 10,512,620 B1 | 12/2019 | Somberg et al. |
| 10,537,588 B2 | 1/2020 | Daemmgen et al. |
| 10,603,316 B2 | 3/2020 | Xiong et al. |
| 10,617,639 B2 | 4/2020 | Helson |
| 10,793,519 B2 | 10/2020 | Somberg et al. |
| 10,799,138 B2 | 10/2020 | Ivaturi et al. |
| 10,888,524 B2 | 1/2021 | Yenkar et al. |
| 10,888,552 B2 | 1/2021 | Rothman |
| 11,286,235 B2 | 3/2022 | Somberg et al. |
| 11,344,518 B2 | 5/2022 | Somberg |
| 11,583,216 B2 | 2/2023 | Ivaturi et al. |
| 11,610,660 B1 | 3/2023 | Devlin et al. |
| 11,696,902 B2 | 7/2023 | Somberg et al. |
| 2007/0009564 A1 | 1/2007 | McClain et al. |
| 2007/0009654 A1 | 1/2007 | Watanabe et al. |
| 2012/0003318 A1 | 1/2012 | Schuler et al. |
| 2014/0235631 A1 | 8/2014 | Bunt et al. |
| 2014/0276404 A1 | 9/2014 | Orlowski |
| 2015/0081010 A1 | 3/2015 | Matheny |
| 2015/0210712 A1 | 7/2015 | Blumberg et al. |
| 2016/0082159 A1 | 3/2016 | Orlowski |
| 2016/0128944 A1 | 5/2016 | Chawrai et al. |
| 2016/0228379 A1 | 8/2016 | Kumar et al. |
| 2016/0271070 A1 | 9/2016 | Singh et al. |
| 2016/0271157 A1 | 9/2016 | Ahmed et al. |
| 2016/0303133 A1 | 10/2016 | Dudley et al. |
| 2016/0317388 A1 | 11/2016 | Bhargava et al. |
| 2017/0049705 A1 | 2/2017 | Mateescu et al. |
| 2017/0087105 A1 | 3/2017 | Yan et al. |
| 2017/0100387 A1 | 4/2017 | Arora et al. |
| 2017/0119627 A1 | 5/2017 | Bhargava et al. |
| 2017/0157076 A1 | 6/2017 | Yacoby-Zeevi et al. |
| 2017/0231885 A1 | 8/2017 | Cremers et al. |
| 2017/0258781 A1 | 9/2017 | Noujaim et al. |
| 2017/0296493 A1 | 10/2017 | Thomas et al. |
| 2017/0348303 A1 | 12/2017 | Bosse et al. |
| 2018/0071390 A1 | 3/2018 | Patel et al. |
| 2019/0307343 A1 | 10/2019 | Ivaturi et al. |
| 2019/0352257 A1 | 11/2019 | Somberg et al. |
| 2019/0380605 A1 | 12/2019 | Ivaturi et al. |
| 2019/0388371 A1 | 12/2019 | Somberg |
| 2019/0389888 A1 | 12/2019 | McChesney et al. |
| 2020/0085771 A1 | 3/2020 | Somberg et al. |
| 2020/0093759 A1 | 3/2020 | Somberg et al. |
| 2020/0226481 A1 | 7/2020 | Sim et al. |
| 2020/0253903 A1 | 8/2020 | Somberg |
| 2020/0338027 A1 | 10/2020 | Somberg |
| 2020/0383941 A1 | 12/2020 | Brelidze et al. |
| 2021/0076959 A1 | 3/2021 | Ivaturi et al. |
| 2021/0107867 A1 | 4/2021 | Somberg et al. |
| 2021/0283049 A1 | 9/2021 | Somberg |
| 2021/0346325 A1 | 11/2021 | Somberg |
| 2022/0142954 A1 | 5/2022 | Somberg |
| 2022/0339130 A1 | 10/2022 | Somberg et al. |
| 2023/0075398 A1 | 3/2023 | Devlin et al. |
| 2023/0172883 A1 | 6/2023 | Kashfian et al. |
| 2023/0187049 A1 | 6/2023 | Devlin et al. |
| 2023/0225664 A1 | 7/2023 | Ivaturi et al. |
| 2023/0225997 A1 | 7/2023 | Kashfian |
| 2023/0248674 A1 | 8/2023 | Kashfian |
| 2023/0255908 A1 | 8/2023 | Kashfian |
| 2023/0255909 A1 | 8/2023 | Kashfian |
| 2023/0270940 A1 | 8/2023 | Devlin et al. |
| 2023/0285273 A1 | 9/2023 | Kashfian |
| 2023/0293426 A1 | 9/2023 | Kashfian |
| 2023/0293455 A1 | 9/2023 | Somberg et al. |
| 2023/0310745 A1 | 10/2023 | Kashfian |
| 2023/0372268 A1 | 11/2023 | Kashfian |
| 2024/0156758 A1 | 5/2024 | Somberg |
| 2024/0261242 A1 | 8/2024 | Kashfian |
| 2025/0140361 A1 | 5/2025 | Kashfian et al. |
| 2025/0152529 A1 | 5/2025 | Somberg et al. |
| 2025/0152530 A1 | 5/2025 | Somberg et al. |
| 2025/0213504 A1 | 7/2025 | Kashfian et al. |

FOREIGN PATENT DOCUMENTS

| | | |
|---|---|---|
| AU | 2003233653 A1 | 12/2003 |
| AU | 2005299693 A1 | 5/2006 |
| AU | 2010231494 A1 | 11/2011 |
| AU | 2013203252 A1 | 8/2013 |
| AU | 2013381856 A1 | 7/2015 |
| AU | 2011289176 B2 | 9/2015 |
| AU | 2015269699 B2 | 12/2016 |
| AU | 2016266020 B2 | 10/2018 |
| AU | 2017357916 A1 | 5/2019 |
| AU | 2016313439 B2 | 10/2019 |
| EP | 0898964 A1 | 3/1999 |
| EP | 1027329 B1 | 2/2003 |
| EP | 1467705 A2 | 10/2004 |
| EP | 1474105 A2 | 11/2004 |
| EP | 1605976 A1 | 12/2005 |
| EP | 2429291 A1 | 3/2012 |
| EP | 1501467 B1 | 5/2012 |
| EP | 2238127 B1 | 8/2012 |
| EP | 2238128 B1 | 8/2012 |
| EP | 2228065 B1 | 12/2012 |
| EP | 2797556 A1 | 11/2014 |
| EP | 2861254 A2 | 4/2015 |
| EP | 3100728 A1 | 12/2016 |

(56) References Cited

FOREIGN PATENT DOCUMENTS

| EP | 2999461 A4 | 2/2017 |
|---|---|---|
| EP | 2714011 B1 | 1/2018 |
| EP | 1951210 B1 | 12/2018 |
| WO | 9921829 A1 | 5/1999 |
| WO | 03020240 A2 | 3/2003 |
| WO | 03059318 A2 | 7/2003 |
| WO | 2004082716 A1 | 9/2004 |
| WO | 2007053393 A2 | 5/2007 |
| WO | 2010132711 A1 | 11/2010 |
| WO | 2012167212 A3 | 2/2013 |
| WO | 2013185764 A2 | 12/2013 |
| WO | 2014133539 A1 | 9/2014 |
| WO | 2014143108 A1 | 9/2014 |
| WO | 2014186843 A1 | 11/2014 |

OTHER PUBLICATIONS (Ivaturi, Vijay et al.) U.S. Appl. No. 16/549,620, filed Aug. 23, 2019, Specification, Claims, Figures and File History as of Dec. 2020, 77 pages (abandoned).
(Ivaturi, Vijay et al.) U.S. Appl. No. 17/003,297, filed Aug. 26, 2020, Specification, Claims, Figures.
(Somberg, John C. et al.) Co-Pending U.S. Appl. No. 16/103,815, filed Aug. 14, 2018, Specification, Claims, Figures.
(Somberg, John C. et al.) Co-Pending U.S. Appl. No. 16/693,310, filed Nov. 24, 2019, Specification, Claims, Figures.
(Somberg, John C. et al.) Co-Pending U.S. Appl. No. 16/693,312, filed Nov. 24, 2019, Specification, Claims, Figures.
(Somberg, John C. et al.) Co-Pending U.S. Appl. No. 16/726,361, filed Dec. 24, 2019, Specification, Claims, Figures.
(Somberg, John) Co-Pending U.S. Appl. No. 16/849,099, filed Apr. 15, 2020, Specification and Claims.
(Somberg, John) Co-Pending U.S. Appl. No. 16/863,567, filed Apr. 30, 2020, Specification and Claims.
(Somberg, John) Co-Pending U.S. Appl. No. 16/946,941, filed Jul. 13, 2020, Specification and Claims.
(Somberg, John) Co-Pending U.S. Appl. No. 17/306,490, filed May 3, 2021, Specification and Claims.
(Somberg, John) Co-Pending U.S. Appl. No. 17/585,190, filed Jan. 26, 2022, Specification and Claims.
U.S. Appl. No. 17/003,297, Non-Final Office Action dated Mar. 14, 2022, 14 pages.
U.S. Appl. No. 17/003,297, Preliminary Amendment filed Dec. 8, 2020, 9 pages.
Barbey, J.T. "Pharmacokinetic, pharmacodynamic, and safety evaluation of an accelerated dose titration regimen of sotalol in healthy middle-aged subjects," Clinical Pharmacology and Therapeutics vol. 66(1) (1999) 91-99.
Batul, S.A., "Intravenous sotalol: Reintroducing a forgotten agent to the electrophysiology therapeutic arsenal," J. Atrial Fibrillation vol. 9(3) (Feb.-Mar. 2017) 1-5.
Blair, Andrew D., et al., Sotalol kinetics in renal insufficiency, Clin. Pharmacol. Ther., 457-463 (Apr. 1981) (7 pages).
Campbell, T.J., "Intravenous sotalol for the treatment of atrial fibrillation and flutter after cardiopulmonary bipass comparison with disopyramide and digoxin in a randomised trial," BR Heart J. (1985) 54:86-90.
Co-Pending U.S. Appl. No. 16/103,815, Final Office Action dated Aug. 13, 2019, 13 pages.
Co-Pending U.S. Appl. No. 16/103,815, Non-Final Office Action dated Feb. 6, 2019, 9 pages.
Co-Pending U.S. Appl. No. 16/103,815, Notice of Allowance dated Oct. 30, 2019, 12 pages.
Co-Pending U.S. Appl. No. 16/103,815, Response to Aug. 13, 2019 Final Office Action, filed Oct. 17, 2019, 10 pages.
Co-Pending U.S. Appl. No. 16/103,815, Response to Dec. 13, 2018 Restriction Requirement, filed Dec. 31, 2018, 3 pages.
Co-Pending U.S. Appl. No. 16/103,815, Response to Feb. 6, 2019 Non-Final Office Action, filed May 6, 2019, 17 pages.
Co-Pending U.S. Appl. No. 16/103,815, Restriction Requirement dated Dec. 13, 2018, 6 pages.
Co-pending U.S. Appl. No. 16/376,706, Final Office Action dated Mar. 27, 2020, 12 pages.
Co-pending U.S. Appl. No. 16/376,706, Non-final Office Action dated Nov. 12, 2019, 12 pages.
Co-pending U.S. Appl. No. 16/376,706, Notice of Allowance and Examiner Initiated Interview Summary dated Jun. 10, 2020, 8 pages.
Co-pending U.S. Appl. No. 16/376,706, Response to Mar. 27, 2020 Final Office Action dated May 27, 2020, 11 pages.
Co-pending U.S. Appl. No. 16/376,706, Response to Nov. 12, 2019 Non-Final Office Action filed Feb. 12, 2020, 10 pages.
Co-Pending U.S. Appl. No. 16/693,310, Final Office Action dated Sep. 3, 2021, 20 pages.
Co-Pending U.S. Appl. No. 16/693,310, Non-Final Office Action dated Feb. 7, 2020, 12 pages.
Co-Pending U.S. Appl. No. 16/693,310, Petition Decision dated Mar. 29, 2021, 2 pages.
Co-Pending U.S. Appl. No. 16/693,310, Response to Feb. 7, 2020 Non-Final Office Action, filed May 5, 2020, 20 pages.
Co-Pending U.S. Appl. No. 16/693,310, Response to Sep. 3, 2021 Final Office Action, dated Feb. 3, 2022, 7 pages.
Co-Pending U.S. Appl. No. 16/693,312, Final Office Action dated Mar. 29, 2021, 14 pages.
Co-Pending U.S. Appl. No. 16/693,312, Non-Final Office Action dated Jan. 7, 2022, 15 pages.
Co-Pending U.S. Appl. No. 16/693,312, Non-Final Office Action dated Oct. 20, 2020, 17 pages.
Co-Pending U.S. Appl. No. 16/693,312, Response to Mar. 29, 2021 Final Office Action, filed Sep. 29, 2021, 13 pages.
Co-Pending U.S. Appl. No. 16/693,312, Response to Oct. 20, 2020 Non-Final Office Action, filed Feb. 22, 2021, 11 pages.
Co-Pending U.S. Appl. No. 16/849,099, Final Office Action dated Feb. 3, 2021, 24 pages.
Co-Pending U.S. Appl. No. 16/849,099, Non-Final Office Action dated Jul. 9, 2020, 19 pages.
Co-Pending U.S. Appl. No. 16/849,099, Notice of Abandonment, Aug. 20, 2021, 2 pages.
Co-Pending U.S. Appl. No. 16/849,099, Response to Jul. 9, 2020 Non-Final Office Action, dated Dec. 9, 2020, 10 pages.
Co-Pending U.S. Appl. No. 16/863,567, Advisory Action dated Dec. 30, 2021, 11 pages.
Co-Pending U.S. Appl. No. 16/863,567, Final Office Action dated Dec. 28, 2020, 17 pages.
Co-Pending U.S. Appl. No. 16/863,567, Final Office Action dated Oct. 26, 2021, 11 pages.
Co-Pending U.S. Appl. No. 16/863,567, Non-Final Office Action and Examiner Initiated Interview Summary dated Jun. 9, 2021, 14 pages.
Co-Pending U.S. Appl. No. 16/863,567, Non-Final Office Action dated Jun. 4, 2020, 18 pages.
Co-Pending U.S. Appl. No. 16/863,567, Response to Jun. 4, 2020 Non-Final Office Action dated Dec. 4, 2020, 10 pages.
Co-Pending U.S. Appl. No. 16/863,567, Response to Jun. 9, 2021 Non-Final Office Action dated Oct. 12, 2021, 8 pages.
Co-Pending U.S. Appl. No. 16/863,567, Response to May 13, 2020 Restriction Requirement, filed May 26, 2020, 44 pages.
Co-Pending U.S. Appl. No. 16/863,567, Response to Oct. 26, 2021 Final Office Action, dated Dec. 10, 2021, 8 pages.
Co-Pending U.S. Appl. No. 16/863,567, Restriction Requirement dated May 13, 2020, 5 pages.
Co-Pending U.S. Appl. No. 16/946,941, Non-Final Office Action dated Feb. 7, 2022, 15 pages.
Co-Pending U.S. Appl. No. 16/946,941, Notice of Allowance dated Apr. 4, 2022, 9 pages.
Co-Pending U.S. Appl. No. 16/946,941, Preliminary Amendment filed Jan. 20, 2021, 3 pages.
Co-Pending U.S. Appl. No. 16/946,941, Response to Feb. 7, 2022 Non-Final Office Action, dated Mar. 8, 2022, 6 pages.
Co-pending U.S. Appl. No. 17/566,840, Non-Final Office Action dated Mar. 23, 2022, 11 pages.

(56) References Cited

OTHER PUBLICATIONS

Co-pending U.S. Appl. No. 17/566,840, Petition Under 37 CFR 1.181 and Preliminary Amendment, dated Feb. 22, 2022, 9 pages.
Co-Pending U.S. Appl. No. 17/585,190, Preliminary Amendment dated Mar. 4, 2022, 4 pages.
Dahmane, E., "Clinical Pharmacology-Driven Research to Optimize Bedside Therapeutics of Sotalol Therapy," Clin Transl Sci (2019) 12:648-656.
Dumas, M. et al., "Variations of sotalol kinetics in renal insufficiency", International Journal of Clinical Pharmacology, Therapy, and Toxicology, Oct. 1, 1989, 27(10), Abstract only.
El-Assaad, I, "Lone Pediatric Atrial Fibrillation in the United States: Analysis of Over 1500 Cases," Pediatr. Cardiol. 38:1004-1009, Springer Publishing, United States (2017).
FDA Highlights of Prescribing Information sotalol hydrochloride injection (2009), https://www.accessdata.fda.gov/drugsatfda_docs/label/2009/022306s000lbl.pdf.
FDA Highlights of Prescribing Information Sotylize (sotalol hydrochloride (2014), https://www.accessdata.fda.gov/drugsatfda_docs/label/2014/205108s000lbl.pdf.
Galloway, C.D., "Development and Validation of a Deep-Learning Model to Screen for Hyperkalemia From the Electrocardiogram," JAMA Cardiol.: E1-E9, Amer. Med. Assoc., United States (Apr. 3, 2019).
Gomes, J.A., "Oral d,l Sotalol reduces the incidence of postoperative atrial fibrillation in coronary artery bypass surgery patients: a randomized, double-blind, placebo-controlled study," J. Am. Coll. Cardio. 34(2):334-9 (1999).
Hannun, A.Y., "Cardiologist-level arrhythmia detection and classification in ambulatory electrocardiograms using a deep neural network," Nature Medicine 25:65-69, Nature Publishing (Jan. 2019).
Ho, D.S.W, et al., "Rapid intravenous infusion of d-l sotalol: time to onset of effects on ventricular refractoriness, and safety," European Heart J. 16:81-86, European Soc. of Cardiology, UK (1995).
Hoffman et al. "Renal Insufficiency and Medication in Nursing Homes" Medicine Deutsches Arzteblatt International 2016; 113: 92-98.
Kerin, Nicholas A., "Intravenous Sotalol: an under used treatment strategy," Cardiology (2018) 140:143-145.
Laer, S., et al., "Development of a safe and effective pediatric dosing regimen for sotalol based population pharmacokinetics and pharmacodynamics in children with supraventricular tachycardia . . . " Pediatric Cardiology vol. 46(7) (2005) 1322-30.
Learn the Heart, "Antiarrhythmic Drug Review," https://www.healio.com/cardiology/learn-the-heart/cardiology-review/topic-reviews/antiarrhythmic-drugs (Year: 2022).
Li, X, "Efficacy of intravenous sotalol for treatment of incessant tachyarrhythmias in children," Amer. J. of Cardiology (2017) 119:1366-1370.
Li, X., "Pediatric dosing of intravenous sotalol based on body surface area in patients with arrhythmia," Pediatr Cardiol (2017) 38:1450-1455.
Lynch, J.J., et al., "Prevention of ventricular fibrillation by dextrorotatory sotalol in conscious canine model of sudden coronary death," Amer. Heart J. vol. 109(5) Part 1, (1985) 949-958.
Marill, K.A., "Meta-analysis of the risk of torsades de pointes in patients treated with intravenous racemic sotalol," Academic Emergency Medicine 8(2):117-124, Wiley, United States (2001).
Neumar, R.W., et al., "Part 8: Adult advanced cardiovascular life support," Circulation (2010) 122, suppl. 3, S729-S767.
Patel, A., "Is Sotalol more effective than standard beta-blockers for prophylaxis of atrial fibrillation during cardiac surgery?" Interactive CardioVascular and Thoracic Surgery 4 (2005) 147-50.
Peters, F.P.J., "Treatment of recent onset atrial fibrillation with intravenous sotalol and/or flecainide," Netherlands J. of Medicine 53:93-96, Elsevier Science B.B., Netherlands (1998).
Peters, N.S., "Post-cardioversion atrial fibrillation: the synthesis of modern concepts?" european Heart J. (2000) 21, 1119-1121.
Radford, D.J., "Atrial Fibrillation in Children," Pediatrics 59(2):250-256, Amer. Acad. of Pediatrics, US (1977).

Sanjuan, R., "Preoperative use of sotalol versus atenolol for atrial fibrillation after cardiac surgery," Ann Thorac Surg (2004) 77:838-43.
Saul, J.P., "Pharmacokinetics and pharmacodynamics of sotalol in a pediatric population with supraventricular and ventricular tachyarrhythmia," Clinical Pharma & Therapeutics 69(3): 145-157 (2001).
Snider, M., et al., "Initial experience with antiarrhythmic medication monitoring by clinical pharmacists in an outpatient setting: a retrospective review," Clinical Therapeutics vol. 31(36) (2009) 1209-1218.
Somberg, J.C., "Gender differences in cardiac repolarization following intravenous sotalol administration," J. Cardiovascular Pharmacology and Therapeutics (2012) 17(1) 86-92.
Somberg, J.C., "QT prolongation and serum sotalol concentration are highly correlated following intravenous and oral sotalol," Cardiology (2010) 116(3):219-25.
Somberg, J.C., et al., "Developing a safe intravenous sotalol dosing regimen," Amer. J. of Therapeutics 17(2010) 365-372.
Somberg, John et al. Model-Informed Development of Sotalol Loading and Dose Escalation Employing an Intravenous Infusion. Cardiol Res. 2020;11(5):294-304.
Sundquist, H.K. et al., "Serum levels and half-life of sotalol in chronic renal failure", Annals of Clinical Research, Dec. 1, 1975, 7(6), Abstract Only.
Thomas, S.P., "Rapid loading of sotalol or amiodarone for management of recent onset symptomatic atrial fibrillation: A randomized, digoxin-controlled trial," Am. Heart J., 147(1) (6 pages) (2004).
Tse, H.F., "Atrial pacing for suppression of early reinitiation of atrial fibrillation after successful internal cardioversion," european Heart J. (2000) 21, 1167-1176.
U.S. Appl. No. 16/376,706 (U.S. Pat. No. 10,799,138), file history Dec. 2020, 151 pages.
Valdes, S.O., "early experience with intravenous sotalol in children with and without congenital heart disease," Heart Rhythm 15(12): 1862-1869, Elsevier Inc., (Jul. 9, 2018).
Yarlagadda, B, et al., "Safety and efficacy of inpatient initiation of dofetilide versus sotalol for atrial fibrillation," J. Atrial Fibrillation vol. 101(4) (2017) 1-5.
Co-Pending U.S. Appl. No. 17/892,301, Restriction Requirement dated Dec. 3, 2024, 6 pages.
Co-pending U.S. Appl. No. 18/107,785, Preliminary Amendment dated Feb. 15, 2024, 10 pages.
Co-pending U.S. Appl. No. 18/121,980, Preliminary Amendment dated Jul. 18, 2023, 6 pages.
Co-Pending U.S. Appl. No. 18/322,111, Preliminary amendment dated Jan. 31, 2024, 7 pages.
Co-Pending U.S. Appl. No. 18/417,748, Preliminary Amendment dated Apr. 22, 2024, 6 pages.
Dwivedi, S.K. et al. "Efficacy of Dual Strategy of Sotalol and Electrical Cardioversion With Balloon Mitral Valvotomy in Persistent Rheumatic Atrial Fibrillation With Mitral Stenosis," Heart, 2012, 98 (Suppl 2): E1-E319, 2 pages.
Falk, Rodney H. et al., Intravenous Dofetilide, a Class III Antiarrhythmic Agent, for the Termination of Sustained Atrial Fibrillation or Flutter, JACC vol. 29, No. 2, 385-90 (Feb. 1997).
FDA "Highlights of Prescribing Information" for sotalol hydrochloride injection, Revised Mar. 2020, 16 pages, https://www.accessdata.fda.gov/drugsatfda_docs/label/2020/022306s005lbrpl.pdf.
Kennedy, D. et al. "Efficacy and Safety of Single Day Loading of Intravenous Sotalol Prior to Direct Current Cardioversion for the Termination of Cardiac Atrial Arrhythmias: An Observational Study," Heart Rhythm, vol. 19, No. 5, May Supplement 2022, 2 pages.
Lai, L. et al. "Intravenous Sotalol Decreases Transthoracic Cardioversion Energy Requirement for Chronic Atrial Fibrillation in Humans: Assessment of the Electrophysiological Effects by Biatrial Basket Electrodes," Journal of the American College of Cardiology, vol. 35, No. 6, 2000, 1435-1441, 8 pages.
Le Coz, F. et al. Pharmacokinetic and pharmacodynamic modeling of the effects of oral and intravenous administrations of dofetilide on ventricular repolarization. Clin Pharmacol Ther 1995; 57:533.

(56) References Cited

OTHER PUBLICATIONS

Malloy-Walton, L. E. et al. "IV Sotalol Use in Pediatric and Congenital Heart Patients: A Multicenter Registry Study," Journal of the American Heart Association, 2022, 11:e024375, 8 pages.
Maragnes, P., et al., "Usefulness of oral sotalol for the treatment of junctional ectopic tachycardia," Int'l J. of Cardiology, 35 (1995) 165-167.
Procainamide Dosage. Drugs.com. Last updated Sep. 13, 2021. 3 pages.
Rasmussen, H.S. et al., Dofetilide, A Novel Class III Antiarrhythmic Agent, J Cardiovasc Pharmacol. 1992;20 Suppl 2:S96-105.
Rosseau, M. F., Cardiac and Hemodynamic Effects of Intravenous Dofetilide in Patients With Heart Failure, Am J Cardiol 2001;87:1250-1254.
Sedgwick, M. et al., Pharmacokinetic and pharmacodynamic effects of UK-68,798, a new potential class III antiarrhythmic drug, Br. J. Clin. Pharmac. (1991), 31, 515-519.
Somberg, et al., "Sotalol versus Amiodarone in Treatment of Atrial Fibrillation," J. Atrial Fibrillation, Feb.-Mar. 2016, vol., Issue 5.
Valdes, S. O. et al. "Intravenous Sotalol for Acute Conversion of Intra-Atrial-Reentrant-Tachycardia in Adults with Congenital Heart Disease," Heart Rhythm, vol. 19, No. 5, May Supplement 2022, 2 pages.
Valdes, S.O. et al. "Intravenous sotalol for the management of postoperative junctional ectopic tachycardia," Heart Rhythm Case Reports, vol. 4, No. 8, Aug. 2018, 375-377, 3 pages.
Von Bergen, N. H. et al. "Outpatient intravenous sotalol load to replace 3-day admission oral sotalol load", Heart Rhythm Case Reports (Jul. 2019), vol. 5, issue 7, p. 382-383.
(Devlin, Jodi) Co-pending U.S. Appl. No. 18/107,785, filed Feb. 9, 2023, Specification, Claims, and Figures.
(Devlin, Jodi) Co-pending U.S. Appl. No. 18/121,980, filed Mar. 15, 2023, Specification, Claims, and Figures.
(Ivaturi, Vijay et al.) U.S. Appl. No. 18/156,092, filed Jan. 18, 2023, Specification, Claims, Figures.
(Kashfian, Brandon Ira et al.) Co-Pending U.S. Appl. No. 17/892,301, filed Aug. 22, 2022, Specification and Claims.
(Kashfian, Brandon Ira) Co-Pending U.S. Appl. No. 18/126,561, filed Mar. 27, 2023, Specification and Claims.
(Kashfian, Brandon Ira) Co-Pending U.S. Appl. No. 18/135,467, filed Apr. 17, 2023, Specification and Claims.
(Kashfian, Brandon Ira) Co-Pending U.S. Appl. No. 18/304,196, filed Apr. 20, 2023, Specification and Claims.
(Kashfian, Brandon Ira) Co-Pending U.S. Appl. No. 18/306,660, filed Apr. 25, 2023, Specification and Claims.
(Kashfian, Brandon Ira) Co-Pending U.S. Appl. No. 18/315,790, filed May 11, 2023, Specification and Claims.
(Kashfian, Brandon Ira) Co-Pending U.S. Appl. No. 18/321,220, filed May 22, 2023, Specification and Claims.
(Kashfian, Brandon Ira) Co-Pending U.S. Appl. No. 18/323,337, filed May 24, 2023, Specification and Claims.
(Kashfian, Brandon Ira) Co-Pending U.S. Appl. No. 18/324,703, filed May 26, 2023, Specification and Claims.
(Kashfian, Brandon Ira) Co-Pending U.S. Appl. No. 18/631,538, filed Apr. 10, 2024, Specification and Claims.
(Somberg, John C. et al.) Co-Pending U.S. Appl. No. 17/861,226, filed Jul. 10, 2022, Specification, Claims, Figures.
(Somberg, John C. et al.) Co-Pending U.S. Appl. No. 18/322,111, filed May 23, 2023, Specification, Claims, Figures.
(Somberg, John) Co-Pending U.S. Appl. No. 18/417,748, filed Jan. 19, 2024, Specification and Claims.
U.S. Appl. No. 17/003,297, Final Office Action dated Jul. 27, 2022, 16 pages.
U.S. Appl. No. 17/003,297, Notice of Allowance dated Oct. 18, 2022, 7 pages.
U.S. Appl. No. 17/003,297, Response to Final Office Action dated Sep. 27, 2022, 12 pages.
U.S. Appl. No. 17/003,297, Response to Mar. 14, 2022 Non-Final Office Action, dated Jun. 15, 2022, 12 pages.
U.S. Appl. No. 18/156,092, Response to Notice to File Missing Parts and Preliminary Amendment, dated Apr. 4, 2023, 6 pages.
Batra, Anjan S., et al., "Junctional ectopic tachycardia: Current strategies for diagnosis and management," Progress in Pediatric Cardiology, 35 (2013) 49-54.
Boriani, G. et al., Increase in QT/QTc dispersion after low energy cardioversion of chronic persistent atrial fibrillation. International Journal of Cardiology. 2004; 95, 245-250.
Borquez, Alejandro A., et al., "Intravenous Sotalol in the Young, Safe and Effective Treatment With Standardized Protocols," JACC: Clinical Elecrophysiology, vol. 6, No. 4, Apr. 2020:425-32 (2020).
Cantillon, D. J. and Amuthan, R. "Atrial Fibrillation", Cleveland Clinic: Center for Continuing Education, Disease Management: https://www.clevelandclinicmeded.com/medicalpubs/diseasemanagement/cardiology/atrial-fibrillation/, Aug. 2018, 18 pages.
CHOC Children's, "Junctional Ectopic Tachycardia (JET) Care Guideline for Cardiovascular Intensive Care Unit (CVICU)," Sep. 18, 2019.
Cilliers, Antionette M., et al., "Junctional ectopic tachycardia in six paediatric patients," Heart; 78:413-415 (1997).
Co-Pending U.S. Appl. No. 16/693,310, Non-Final Office Action dated Jul. 21, 2022, 16 pages.
Co-Pending U.S. Appl. No. 16/693,310, Notice of Allowance dated Mar. 9, 2023, 7 pages.
Co-Pending U.S. Appl. No. 16/693,310, Response to Jul. 21, 2022 Non-Final Office Action including Rule 132 Affidavit, dated Jan. 20, 2023, 15 pages.
Co-Pending U.S. Appl. No. 16/693,312, Final Office Action dated Feb. 22, 2024, 23 pages.
Co-Pending U.S. Appl. No. 16/693,312, Final Office Action dated Oct. 14, 2022, 16 pages.
Co-Pending U.S. Appl. No. 16/693,312, Interview Summary dated Feb. 22, 2024, 1 page.
Co-Pending U.S. Appl. No. 16/693,312, Non-Final Office Action dated Aug. 19, 2024, 15 pages.
Co-Pending U.S. Appl. No. 16/693,312, Non-Final Office Action dated Nov. 1, 2023, 18 pages.
Co-Pending U.S. Appl. No. 16/693,312, Response to Feb. 22, 2024 Final Office Action, dated May 14, 2024, 10 pages.
Co-Pending U.S. Appl. No. 16/693,312, Response to Jan. 7, 2022 Non-Final Office Action, dated Jul. 6, 2022, 8 pages.
Co-Pending U.S. Appl. No. 16/693,312, Response to Nov. 1, 2023 Non-Final Office Action, dated Feb. 1, 2024, 11 pages.
Co-Pending U.S. Appl. No. 16/693,312, Response to Oct. 14, 2022 Final Office Action dated Apr. 14, 2023, 16 pages.
Co-Pending U.S. Appl. No. 16/693,312, Rule 132 Affidavit dated Feb. 1, 2024, 7 pages.
Co-Pending U.S. Appl. No. 17/306,490, Non-Final Office Action dated Jun. 7, 2024, 50 pages.
Co-Pending U.S. Appl. No. 17/306,490, Preliminary Amendment filed Dec. 7, 2022, 38 pages.
Co-Pending U.S. Appl. No. 17/306,490, Response to Jun. 7, 2024 Non-Final Office Action, dated Dec. 6, 2024, 9 pages.
Co-pending U.S. Appl. No. 17/566,840, Notice of Allowance dated Jul. 25, 2022, 7 pages.
Co-pending U.S. Appl. No. 17/566,840, Notice of Allowance dated Nov. 9, 2022, 7 pages.
Co-pending U.S. Appl. No. 17/566,840, Response to Mar. 23, 2022 Non-Final Office Action, dated Jul. 7, 2022, 10 pages.
Co-Pending U.S. Appl. No. 17/585,190, Restriction Requirement dated Oct. 19, 2023, 5 pages.
Co-Pending U.S. Appl. No. 17/861,226, Non-Final Office Action dated Jul. 16, 2024, 17 pages.
Co-Pending U.S. Appl. No. 17/861,226, Preliminary Amendment dated Jul. 10, 2022, 4 pages.
Co-Pending U.S. Appl. No. 17/861,226, Response to Jul. 16, 2024 Non-Final Office Action, dated Dec. 16, 2024, 9 pages.
(Kashfian, Brandon Ira et al.) Co-Pending U.S. Appl. No. 19/009,774, filed Jan. 3, 2025, Specification, Drawings, and Claims.
(Kashfian, Brandon Ira et al.) Co-Pending U.S. Appl. No. 19/080,585, filed Mar. 14, 2025, Specification and Claims.
(Somberg, John et al.) Co-Pending U.S. Appl. No. 19/019,556, filed Jan. 14, 2025, Specification and Claims.

(56) References Cited

OTHER PUBLICATIONS (Somberg, John et al.) Co-Pending U.S. Appl. No. 19/022,878, filed Jan. 15, 2025, Specification and Claims.

Bianconi, L. et al., Comparison of intravenously administered dofetilide versus amiodarone in the acute termination of atrial fibrillation and flutter, European Heart Journal (2000) 21, 1265-1273, 9 pages.

Co-Pending U.S. Appl. No. 16/693,312, Response to Aug. 19, 2024 Non-Final Office Action, dated Dec. 19, 2024, 8 pages.

Co-Pending U.S. Appl. No. 17/306,490, Final Office Action dated Mar. 11, 2025, 13 pages.

Co-Pending U.S. Appl. No. 17/861,226, Final Office Action dated Mar. 21, 2025, 24 pages.

Co-Pending U.S. Appl. No. 17/861,226, Interview Summary dated Jan. 7, 2025, 2 pages.

Co-Pending U.S. Appl. No. 17/892,301, Response to Dec. 3, 2024 Restriction Requirement, dated Mar. 3, 2025, 7 pages.

Co-Pending U.S. Appl. No. 17/892,301, Non-Final Office Action dated Mar. 24, 2025, 11 pages.

Co-Pending U.S. Appl. No. 19/019,556, Preliminary Amendment dated Jan. 14, 2025, 4 pages.

DAILYMED Website, TIKOSYN (dofetilide) Capsules, https://dailymed.nlm.nih.gov/dailymed/fda/fdaDrugXsl.cfm?setid=02438044-d6a3-49e9-a1ac-3aad21ef2c8c (Year: 1999), 21 pages.

Kerin, N. Z. and Jacob, S., The Efficacy of Sotalol in Preventing Postoperative Atrial Fibrillation: A Meta-Analysis, The American Journal of Medicine, vol. 124, No. 9, Sep. 2011, 9 pages.

(Kashfian, Brandon Ira et al.) Co-Pending U.S. Appl. No. 19/277,199, filed Jul. 22, 2025, Specification and Claims.

Co-Pending U.S. Appl. No. 17/306,490, Non-Final Office Action dated Jul. 15, 2025, 12 pages.

Co-Pending U.S. Appl. No. 17/306,490, Response to Mar. 11, 2025 Final Office Action, dated Jun. 26, 2025, 6 pages.

Co-Pending U.S. Appl. No. 17/861,226, Response to Mar. 21, 2025 Final Office Action, dated Jun. 23, 2025, 11 pages.

Co-Pending U.S. Appl. No. 17/892,301, Notice of Allowance dated Jul. 11, 2025, 8 pages.

Co-Pending U.S. Appl. No. 17/892,301, Response to Mar. 24, 2025 Non-Final Office Action, dated Jun. 24, 2025, 9 pages.

Co-pending U.S. Appl. No. 18/107,785, Non-Final Office Action dated May 8, 2025, 9 pages.

SOTALOL HYDROCHLORIDE DOSING

CROSS-REFERENCE TO RELATED APPLICATIONS

This application is a Continuation of and claims priority to and the benefit of the filing date of U.S. application Ser. No. 16/946,941, filed Jul. 13, 2020; which application is a Continuation-in-Part (CIP) of U.S. application Ser. No. 16/863,567, filed Apr. 30, 2020; which '567 Application claims priority to and the benefit of the filing date of U.S. Provisional Application No. 63/009,511, filed Apr. 14, 2020; which '567 Application is a CIP of U.S. application Ser. No. 16/693,310, filed Nov. 24, 2019; and which '310 Application is a CIP of U.S. application Ser. No. 16/103,815, filed Aug. 14, 2018, now U.S. Pat. No. 10,512,620, which patent issued Dec. 24, 2019; the '567 Application is also a CIP of U.S. application Ser. No. 16/693,312, filed Nov. 24, 2019; the '312 Application is a Continuation of the '815 Application; the '941 Application is also a CIP of U.S. application Ser. No. 16/849,099, filed Apr. 15, 2020; which '099 Application claims priority to and the benefit of the filing date of U.S. Provisional Application No. 62/987,832, filed Mar. 10, 2020, the disclosures of each of which are hereby incorporated herein by reference in their entireties.

FIELD OF THE INVENTION

The present invention provides novel methods of initiating and escalating sotalol hydrochloride in patients in need thereof.

BACKGROUND OF THE INVENTION

Sotalol hydrochloride ("sotalol") is Vaughan Williams Class III anti-arrhythmic drug that prolongs cardiac action potential duration by blocking the outward potassium channel IKr (rapid potassium rectifier current), thereby prolonging repolarization time.

Although sotalol is effective at treating or preventing atrial fibrillation, atrial flutter, and combinations thereof, sotalol's mechanism of action is both anti-arrhythmic and pro-arrhythmic. Too much sotalol too fast can lead to excessive prolongation of repolarization time giving rise to life threatening arrhythmias, especially Torsade de Pointes ventricular tachycardia (Tdp). Thus, it is well understood in the art, that during sotalol's initial loading, or in a dose escalation intervention, it is critical to monitor a subject's QTc interval to avoid excessive QTc prolongation.

Due to sotalol's potential to induce arrhythmia, the FDA has mandated in-hospital QTc monitoring for at least three days upon initial sotalol hydrochloride loading and for dose escalation. Although this extended hospital stay is effective at reducing subject risk, maintaining the subject in a telemetry unit for three days is extremely expensive, making sotalol a less desirable treatment choice in a managed care environment. A need therefore exists to develop methods of reducing the length of hospital stay required to safely and efficaciously administer sotalol to subjects in need thereof.

SUMMARY OF THE INVENTION

Accordingly, in an aspect, the present invention provides a novel method of initiating or escalating sotalol hydrochloride in a patient in need thereof.

In another aspect, the present invention provides a method of reducing the hospitalization time required for initiating and escalating sotalol hydrochloride in a patient in need thereof.

In another aspect, the present invention provides a method of treating AFIB/AFL, comprising: initiating or escalating sotalol hydrochloride in a patient in need thereof.

These and other aspects, which will become apparent during the following detailed description, have been achieved by the inventors' discovery that oral sotalol can be intravenously initiated or escalated.

DETAILED DESCRIPTION OF THE INVENTION

All references cited herein are hereby incorporated in their entirety herein by reference.

AFIB is atrial fibrillation.

AFL is atrial flutter.

AFIB/AFL=atrial fibrillation and/or atrial flutter.

IV is intravenous.

PO means "per os" and refers to an oral dosing regimen.

BID means "bis in die" and means twice a day.

QD means "quaque die" and means once a day.

Patient (or subject) refers to a human patient.

BP is blood pressure.

HR is heart rate.

Renally impaired refers to patients having creatine clearance rates of ≤60 mL/min.

Escalation or uptitration means increasing the oral sotalol dosage of a patient (e.g., from 80 to 120 or from 120 to 160 BID).

QT is the interval measured from the start of the Q wave or the QRS complex, to the end of the T wave, where the Q wave corresponds to the beginning of ventricular depolarization and the T wave end corresponds to the end of ventricular repolarization.

QTc is the calculated interval that represents the QT interval corrected for heart rate and can be derived by simple mathematical correlation of the QT interval and the heart rate.

ΔQTc is the difference between a QTc measurement taken prior to the start of IV sotalol and a QTc measured after the start of IV sotalol (e.g., during loading or maintenance).

Sotalol and sotalol hydrochloride (used interchangeably herein) refer to d,l-sotalol hydrochloride which has been approved by the FDA for intravenous administration over 5 hours or oral administration (e.g., 80 mg, 120 mg, and 160 mg tablets).

In an example, sotalol injection is supplied in 10 mL single-dose vials, each containing 150 mg of sotalol hydrochloride as a clear solution (15 mg/mL).

Sotalol hydrochloride is contraindicated in patients with:
Sinus bradycardia (<50 bpm), sick sinus syndrome or second or third degree AV block without a pacemaker
Congenital or acquired long QT syndromes, QT interval >450 ms
Cardiogenic shock, decompensated heart failure
Serum potassium <4 mEq/L
Bronchial asthma or related bronchospastic conditions
Known hypersensitivity to sotalol Hospital refers to a medical facility staffed and equipped to provide continuous ECG monitoring and cardiac resuscitation to patients, if needed. Typically, the medical personnel are trained in the management of serious ventricular arrhythmias.

Reducing or shortening the length of a hospital stay refers to reducing/shortening the length of time a patient is admitted for oral sotalol initiation or escalation. For example, a patient would typically require a 3-day (72 hour) stay to be initiated/escalated on oral sotalol.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; or improving a subject's physical or mental well-being. The treatment or amelioration of symptoms can be based on objective or subject parameters, including the results of a physical examination, neuropsychiatric examinations, or psychiatric evaluation.

Sotalol Indications

Delay in Recurrence of Atrial Fibrillation/Atrial Flutter: Sotalol is indicated for the maintenance of normal sinus rhythm (delay in time to recurrence of atrial fibrillation/atrial flutter (AFIB/AFL)) in patients with symptomatic AFIB/AFL who are currently in sinus rhythm.

Life-Threatening Ventricular Arrhythmia: Sotalol is also indicated for the treatment of life-threatening ventricular tachycardia.

For either indication, intravenous sotalol, when used as a loading dose, achieves steady state concentration faster compared to the conventional oral dosing (e.g., typically 3-days for a non-renally impaired patient).

Typically, IV sotalol is diluted for infusion. For example, IV sotalol can be diluted in saline, 5% dextrose in water (D5W), or Ringer's lactate. The dilution volume chosen is one that is convenient for administration and consistent with fluid restriction. A volumetric infusion pump can be used to administer the IV sotalol.

Typically, other antiarrhythmic therapy is withdrawn prior to starting sotalol.

The IV loading dose depends on the target oral dose and creatinine clearance of the patient indicated for oral sotalol. The dosing interval for oral administration of sotalol and the minimum delay between the end of the infusion and the first oral dose also depend on renal function.

Thus, in an aspect, the present invention provides a novel method of initiating or escalating sotalol therapy, comprising: administering to a patient in need thereof (a patient for whom sotalol is indicated) an IV and oral sotalol dosage based on the patient's creatine clearance (CrCl mL/min), wherein the dosages and timing are selected from Table 1.

The Cockcroft-Gault formulas for creatine clearance (CrCl) are:

$$CrCl\ (male) = ((140 - age) \times weight\ in\ kg)/(serum\ creatinine \times 72)$$

$$CrCl\ (female) = CrCl\ (male) \times 0.85$$

Recommended starting dose (80 mg) is the FDA recommended dosage. A physician can select to start a patient on a higher dosage (e.g., 120 mg), if deemed appropriate.

Minimum delay to first oral dose is the time from the end of the IV infusion to the first oral dose.

Oral dosing interval refers to the time between oral dosages. 12 h is B.I.D. (or BID). 24 h is QD.

The IV load, as shown in Table 1, is typically administered (infused) over 1 hour. Additional examples include 50-70 minutes. Further examples include 50, 51, 52, 53, 54, 55, 56, 57, 58, 59, 60, 61, 62, 63, 64, 65, 66, 67, 68, 69, and 70 minutes.

Examples of the IV load for a target oral dose of 80 mg include 55-85 mg. For example, Table 1 shows that the IV loads for initiation of a target dose of 80 mg are 60 mg (>90 CrCl), 82.5 mg (60-90 CrCl), and 75 mg (30-60 CrCl and 10-30 CrCl). Further examples include 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85 mg.

Examples of the IV load for a target oral dose of 120 mg include 75-115 mg. For example, Table 1 shows that the IV loads for initiation of a target dose of 120 mg are 90 mg (>90 CrCl), 125 mg (60-90 CrCl), and 112.5 mg (30-60 CrCl and 10-30 CrCl). Additional examples of the IV load for the target dose of 120 mg include 75-135 mg. Further examples include 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135 mg.

Further, for example, Table 1 shows that the IV loads for escalation from 80 to 120 mg are 75 mg (>90 CrCl), and 82.5 (60-90 CrCl, 30-60 CrCl, and 10-30 CrCl). Additional examples of the IV load for escalation to 120 mg include 65-90 mg. Further examples include 65, 66, 67, 68, 69, 70, 71, 72, 73, 74, 75, 76, 77, 78, 79, 80, 81, 82, 83, 84, 85, 86, 87, 88, 89, and 90 mg.

Examples of the IV load for a target oral dose of 160 mg include 80-150 mg. For example, Table 1 shows that the IV loads for escalation from 120 to 160 mg are 90 mg (>90 CrCl), and 105 (60-90 CrCl, 30-60 CrCl, and 10-30 CrCl). Additional examples of the IV load for escalation to 160 mg include 80-120 mg. Further examples include 80, 81, 82, 83,

TABLE 1

IV Sotalol Loading Dosage and Initiation-Escalation Protocol

| Creatinine Clearance* (mL/min) | IV loading dose (1 h infusion) when the oral dose is going from . . . | | | | Minimum delay to first oral dose (h) | Oral dosing interval (h) |
|---|---|---|---|---|---|---|
| | Sotalol Initiation | |سotalol Escalation | | | |
| | 0 to 80 mg** | 0 to 120 mg | 80 to 120 mg | 120 to 160 mg | | |
| >90 | 60 | 90 | 75 | 90 | 4 | 12 |
| >60-90 | 82.5 | 125 | 82.5 | 105 | 4 | 12 |
| >30-60 | 75 | 112.5 | 82.5 | 105 | 6 | 24 |
| 10-30 | 75 | 112.5 | 82.5 | 105 | 12 | 48 |

*Calculated using Cockcroft-Gault formula
**Recommended starting dose 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 and 150 mg.

As can be seen in Table 1, the time of when oral dosing begins depends on the CrCl of the patient. Oral dosing for CrCl of >90 and 60-90 typically begins 4 h after IV infusion (e.g., 5 hours after the start of a 1 h IV). Oral dosing for CrCl of 30-60 typically begins 6 h after IV infusion (e.g., 7 h after the start of a 1 h IV). Oral dosing for CrCl of 10-30 typically begins 12 h after IV infusion (e.g., 13 h after the start of a 1 h IV).

Additional examples of when the oral dosing begins for a CrCl of >90 include 2-6 h after completion of infusion. Further examples include 2, 3, 4, 5, to 6 h.

Additional examples of when the oral dosing begins for a CrCl of 60-90 include 2-6 h after completion of infusion. Further examples include 2, 3, 4, 5, to 6 h.

Additional examples of when the oral dosing begins for a CrCl of 30-60 include 4-8 h after completion of infusion. Further examples include 4, 5, 6, 7, to 8 h.

Additional examples of when the oral dosing begins for a CrCl of 10-30 include 10-14 h after completion of infusion. Further examples include 10, 11, 12, 13, to 14 h.

As can be seen in Table 1, the oral dosing interval depends on the CrCl of the patient. Oral dosing for CrCl of >90 and 60-90 is typically every 12 h (BID). Oral dosing for CrCl of 30-60 is typically every 24 h (QD). Oral dosing for CrCl of 10-30 is typically every 48 h.

Additional examples of the oral dosing interval for a CrCl of >90 include 8-16 h after completion of infusion. Further examples include 8, 9, 10, 11, 12, 13, 14, 15, to 16 h.

Additional examples of the oral dosing interval for a CrCl of 60-90 include 8-16 h after completion of infusion. Further examples include 8, 9, 10, 11, 12, 13, 14, 15, to 16 h.

Additional examples of the oral dosing interval for a CrCl of 30-60 include 20-28 h after completion of infusion. Further examples include 20, 21, 22, 23, 24, 25, 26, 27, to 28 h.

Additional examples of when the oral dosing begins for a CrCl of 10-30 include 40-56 h after completion of infusion. Further examples include 40, 41, 42, 43, 44, 45, 46, 47, 48, 49, 50, 51, 52, 53, 54, 55, to 56 h.

In another aspect, the present invention provides a novel method of initiating or escalating sotalol therapy, comprising: administering to a patient in need thereof an IV and oral dosage of sotalol selected by a physician, wherein the patient's physician selects the IV and oral dosages based on the patient's CrCl as defined in Table 1.

In another aspect, the present invention provides a novel method of initiating or escalating oral sotalol therapy, comprising:
  A intravenously (IV) administering sotalol hydrochloride over a period of 1 hour, to a patient in need thereof, wherein the IV dosage is selected from dosages I(a)-IV(d):
    I for patients having creating clearance (CrCl) of >90 mL/min;
      (a) 60 mg for a patient naïve to sotalol and having a target of 80 mg;
      (b) 90 mg for a patient naïve to sotalol and having a target of 120 mg;
      (c) 75 mg for a patient previously receiving 80 mg of sotalol;
      (d) 90 mg for a patient previously receiving 120 mg of sotalol;
    II for patients having creating clearance (CrCl) of >60-90 mL/min;
      (a) 82.5 mg for a patient naïve to sotalol and having a target of 80 mg;
      (b) 125 mg for a patient naïve to sotalol and having a target of 120 mg;
      (c) 82.5 mg for a patient previously receiving 80 mg of sotalol;
      (d) 105 mg for a patient previously receiving 120 mg of sotalol;
    III for patients having creating clearance (CrCl) of >30-60 mL/min;
      (a) 75 mg for a patient naïve to sotalol and having a target of 80 mg;
      (b) 112.5 mg for a patient naïve to sotalol and having a target of 120 mg;
      (c) 82.5 mg for a patient previously receiving 80 mg of sotalol;
      (d) 105 mg for a patient previously receiving 120 mg of sotalol;
    IV for patients having creating clearance (CrCl) of 10-30 mL/min;
      (a) 75 mg for a patient naïve to sotalol and having a target of 80 mg;
      (b) 112.5 mg for a patient naïve to sotalol and having a target of 120 mg;
      (c) 82.5 mg for a patient previously receiving 80 mg of sotalol; and,
      (d) 105 mg for a patient previously receiving 120 mg of sotalol; and,
  B orally administering sotalol hydrochloride to the patient at a dosage and interval selected from (I)-(IX):
    I 80 mg BID, starting 4 hours after completion of IV doses I(a) and II(a);
    II 120 mg BID, starting 4 hours after completion of IV doses I(b), I(c), II(b), and II(c);
    III 160 mg BID, starting 4 hours after completion of IV doses I(d) and II(d);
    IV 80 mg QD, starting 6 hours after completion of IV dose III(a);
    V 120 mg QD, starting 6 hours after completion of IV doses III(b) and III(c);
    VI 160 mg QD, starting 6 hours after completion of IV dose III(d);
    VII 80 mg once every 48 h, starting 12 hours after completion of IV dose IV(a);
    VIII 120 mg once every 48 h, starting 12 hours after completion of IV doses IV(b) and IV(c); and,
    IX 160 mg once every 48 h, starting 12 hours after completion of IV dose IV(d).

In another aspect, the present invention provides a novel method of initiating or escalating oral sotalol therapy, comprising:
  A intravenously (IV) administering sotalol hydrochloride over a period of 1 hour, to a patient in need thereof, wherein the IV dosage is selected from dosages I(a)-IV(d):
    I for patients having creating clearance (CrCl) of >90 mL/min;
      (a) 60 mg for a patient naïve to sotalol and having a target of 80 mg;
      (b) 90 mg for a patient naïve to sotalol and having a target of 120 mg;
      (c) 75 mg for a patient previously receiving 80 mg of sotalol;

(d) 90 mg for a patient previously receiving 120 mg of sotalol;
II for patients having creating clearance (CrCl) of >60-90 mL/min;
  (a) 82.5 mg for a patient naïve to sotalol and having a target of 80 mg;
  (b) 125 mg for a patient naïve to sotalol and having a target of 120 mg;
  (c) 82.5 mg for a patient previously receiving 80 mg of sotalol;
  (d) 105 mg for a patient previously receiving 120 mg of sotalol;
III for patients having creating clearance (CrCl) of >30-60 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol;
  (d) 105 mg for a patient previously receiving 120 mg of sotalol;
IV for patients having creating clearance (CrCl) of 10-30 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol; and,
  (d) 105 mg for a patient previously receiving 120 mg of sotalol; and,
B orally administering sotalol hydrochloride to the patient at a dosage and interval selected from (I)-(IX):
  I 80 mg BID, starting 3-5 hours after completion of IV doses I(a) and II(a);
  II 120 mg BID, starting 3-5 hours after completion of IV doses I(b), I(c), II(b), and II(c);
  III 160 mg BID, starting 3-5 hours after completion of IV doses I(d) and II(d);
  IV 80 mg QD, starting 5-7 hours after completion of IV dose III(a);
  V 120 mg QD, starting 5-7 hours after completion of IV doses III(b) and III(c);
  VI 160 mg QD, starting 5-7 hours after completion of IV dose III(d);
  VII 80 mg once every 48 h, starting 10-14 hours after completion of IV dose IV(a);
  VIII 120 mg once every 48 h, starting 10-14 hours after completion of IV doses IV(b) and IV(c); and,
  IX 160 mg once every 48 h, starting 10-14 hours after completion of IV dose IV(d).

In another aspect, the present invention provides a novel method of initiating or escalating oral sotalol therapy, comprising:
  A intravenously (IV) administering sotalol hydrochloride over a period of 1 hour, to a patient in need thereof, wherein the IV dosage is selected from dosages I(a)-IV(d):
  I for patients having creating clearance (CrCl) of >90 mL/min;
    (a) 50-70 mg for a patient naïve to sotalol and having a target of 80 mg;
    (b) 80-100 mg for a patient naïve to sotalol and having a target of 120 mg;
    (c) 65-85 mg for a patient previously receiving 80 mg of sotalol;

(d) 80-100 mg for a patient previously receiving 120 mg of sotalol;
II for patients having creating clearance (CrCl) of >60-90 mL/min;
  (a) 72.5-92.5 mg for a patient naïve to sotalol and having a target of 80 mg;
  (b) 115-135 mg for a patient naïve to sotalol and having a target of 120 mg;
  (c) 72.5-92.5 mg for a patient previously receiving 80 mg of sotalol;
  (d) 95-115 mg for a patient previously receiving 120 mg of sotalol;
III for patients having creating clearance (CrCl) of >30-60 mL/min;
  (a) 65-85 mg for a patient naïve to sotalol and having a target of 80 mg;
  (b) 102.5-122.5 mg for a patient naïve to sotalol and having a target of 120 mg;
  (c) 72.5-92.5 mg for a patient previously receiving 80 mg of sotalol;
  (d) 95-115 mg for a patient previously receiving 120 mg of sotalol;
IV for patients having creating clearance (CrCl) of 10-30 mL/min;
  (a) 65-85 mg for a patient naïve to sotalol and having a target of 80 mg;
  (b) 102.5-122.5 mg for a patient naïve to sotalol and having a target of 120 mg;
  (c) 72.5-92.5 mg for a patient previously receiving 80 mg of sotalol; and,
  (d) 95-115 mg for a patient previously receiving 120 mg of sotalol; and,
B orally administering sotalol hydrochloride to the patient at a dosage and interval selected from (I)-(IX):
  I 80 mg BID, starting 4 hours after completion of IV doses I(a) and II(a);
  II 120 mg BID, starting 4 hours after completion of IV doses I(b), I(c), II(b), and II(c);
  III 160 mg BID, starting 4 hours after completion of IV doses I(d) and II(d);
  IV 80 mg QD, starting 6 hours after completion of IV dose III(a);
  V 120 mg QD, starting 6 hours after completion of IV doses III(b) and III(c);
  VI 160 mg QD, starting 6 hours after completion of IV dose III(d);
  VII 80 mg once every 48 h, starting 12 hours after completion of IV dose IV(a);
  VIII 120 mg once every 48 h, starting 12 hours after completion of IV doses IV(b) and IV(c); and,
  IX 160 mg once every 48 h, starting 12 hours after completion of IV dose IV(d).

In another aspect, the present invention provides a novel method of initiating or escalating oral sotalol therapy, comprising:
  A intravenously (IV) administering sotalol hydrochloride over a period of 40-80 minutes, to a patient in need thereof, wherein the IV dosage is selected from dosages I(a)-IV(d):
  I for patients having creating clearance (CrCl) of >90 mL/min;
    (a) 50-70 mg for a patient naïve to sotalol and having a target of 80 mg;
    (b) 80-100 mg for a patient naïve to sotalol and having a target of 120 mg;
    (c) 65-85 mg for a patient previously receiving 80 mg of sotalol;

(d) 80-100 mg for a patient previously receiving 120 mg of sotalol;
II for patients having creating clearance (CrCl) of >60-90 mL/min;
  (a) 72.5-92.5 mg for a patient naïve to sotalol and having a target of 80 mg;
  (b) 115-135 mg for a patient naïve to sotalol and having a target of 120 mg;
  (c) 72.5-92.5 mg for a patient previously receiving 80 mg of sotalol;
  (d) 95-115 mg for a patient previously receiving 120 mg of sotalol;
III for patients having creating clearance (CrCl) of >30-60 mL/min;
  (a) 65-85 mg for a patient naïve to sotalol and having a target of 80 mg;
  (b) 102.5-122.5 mg for a patient naïve to sotalol and having a target of 120 mg;
  (c) 72.5-92.5 mg for a patient previously receiving 80 mg of sotalol;
  (d) 95-115 mg for a patient previously receiving 120 mg of sotalol;
IV for patients having creating clearance (CrCl) of 10-30 mL/min;
  (a) 65-85 mg for a patient naïve to sotalol and having a target of 80 mg;
  (b) 102.5-122.5 mg for a patient naïve to sotalol and having a target of 120 mg;
  (c) 72.5-92.5 mg for a patient previously receiving 80 mg of sotalol; and,
  (d) 95-115 mg for a patient previously receiving 120 mg of sotalol; and,
B orally administering sotalol hydrochloride to the patient at a dosage and interval selected from (I)-(IX):
  80 mg BID, starting 3-5 hours after completion of IV doses I(a) and II(a);
  II 120 mg BID, starting 3-5 hours after completion of IV doses I(b), I(c), II(b), and II(c);
  III 160 mg BID, starting 3-5 hours after completion of IV doses I(d) and II(d);
  IV 80 mg QD, starting 5-7 hours after completion of IV dose III(a);
  V 120 mg QD, starting 5-7 hours after completion of IV doses III(b) and III(c);
  VI 160 mg QD, starting 5-7 hours after completion of IV dose III(d);
  VII 80 mg once every 48 h, starting 10-14 hours after completion of IV dose IV(a);
  VIII 120 mg once every 48 h, starting 10-14 hours after completion of IV doses IV(b) and IV(c); and,
  IX 160 mg once every 48 h, starting 10-14 hours after completion of IV dose IV(d).

In another aspect, the patient is indicated for chronic, but not acute sotalol therapy.

In another aspect, the patient is under ECG monitoring.

In another aspect, the patient is in a hospital for the IV loading and at least 2 oral dosages.

In another aspect, the patient experiences 3 sotalol steady state $C_{max}$ in less than 24 hours, which allows for a QTc interval of the subject that corresponds to the full concentration effect of sotalol to be assessed in less than 24 hours (as opposed to the typical ~72 hours required for oral initiation and/or escalation).

In another aspect, the patient is considered to have been initiated/escalated on oral sotalol after having experienced 3 sotalol steady state $C_{max}$.

In a patient having a CrCl of >60 mL, oral at least 5-6 doses of oral sotalol (BID) are recommended before the patient is able to be discharged. In a patient having a CrCl of 40-60 mL, oral at least 5-6 doses of oral sotalol (QD) are recommended before the patient is able to be discharged. Currently, patients with a CrCl<40 mL/min are not recommended for oral sotalol.

In another aspect, the patient is considered to have been initiated/escalated on oral sotalol after having received at least at least 2, 3, or 4 oral dosages.

In another aspect, the patient is considered to have been initiated/escalated on oral sotalol after having received at least at least 2 oral dosages and the patient's CrCl is >90 mL/min. In another example, the patient received 3 oral dosages. In another example, the patient received 4 oral dosages.

In another aspect, the patient is considered to have been initiated/escalated on oral sotalol after having received at least at least 2 oral dosages and the patient's CrCl is >60-90 mL/min. In another example, the patient received 3 oral dosages. In another example, the patient received 4 oral dosages.

In another aspect, the patient is considered to have been initiated/escalated on oral sotalol after having received at least at least 2 oral dosages and the patient's CrCl is >30-60 mL/min. In another example, the patient received 3 oral dosages. In another example, the patient received 4 oral dosages.

In another aspect, the patient is considered to have been initiated/escalated on oral sotalol after having received at least at least 2 oral dosages and the patient's CrCl is 10-30 mL/min. In another example, the patient received 3 oral dosages. In another example, the patient received 4 oral dosages.

In another aspect, the method of initiating or escalating oral sotalol therapy, further comprises: prior to IV loading, measuring the patient's serum creatine level and calculating the patient's Creatine Clearance (CrCl) using the Cockcroft-Gault formula.

In another aspect, the patient's baseline QTc is measured prior to initiation or escalation.

In another aspect, only patients having a QTc<450 ms are initiated or escalated.

In another aspect, the patient's QTc interval is measured every 15 minutes during IV infusion.

In another aspect, the patient's QTc interval is measured for 2-4 hours after the first oral dosage.

In another aspect, the patient's QTc interval is measured for 2-4 hours after the second oral dosage for patients having a CrCl of ≥60 mL/min.

In another aspect, if the patient's QTc interval is >500 ms or if the ΔQTc is 20% when initiating an 80 mg oral dosage, the method is discontinued.

In another aspect, the present invention provides a method of treating AFIB/AFL, comprising: initiating or escalating sotalol hydrochloride as described herein in a patient in need thereof (e.g., see Table 1).

In another aspect, the method reduces the overall time of hospitalization of the patient (compared to a patient initiated or escalated with only oral sotalol).

In another aspect, the patient being initiated/escalated on sotalol and having a CrCl of >60 mL/min is able to be discharged from the hospital is less than the standard 72-hours required for only oral sotalol initiation/escalation. For example, the patent is able to be discharged (or is discharged) from 18-48 hours after IV initiation. Additional examples include from 18-36 hours, from 18-24 hours, and from 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, to 48 hours after IV initiation.

In another aspect, the patient being initiated/escalated on sotalol and having a CrCl of from 10-60 (renally impaired) is able to be discharged from the hospital is less than the standard 5-6 days (5-6 dosages QD) required for only oral sotalol initiation/escalation and having a CrCl of 40-60 mL/min. For example, the patent is able to be discharged (or is discharged) from 24-96 hours after IV initiation. Additional examples include from 24-72 hours, from 36-48 hours, and from 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, to 72 hours after IV initiation.

In another aspect, the oral therapy is maintained at the patient's physician's discretion. For example, the oral therapy can be continued for days, weeks, or months.

In another aspect, the patient's QTc is monitored via electrocardiography.

In another aspect, the patient's QTc is measured at baseline (prior to sotalol administration) and then measured periodically thereafter (e.g., every 15 or 30 minutes during loading). The QTc can be measured at other intervals if more (shorter time period) or less data (longer time periods) data is desired.

In another aspect, the HR and BP the patient is monitored every 15 minutes (or 30 minutes) during IV administration. If a BP below 90 mmHg and HR <50 bpm are observed, then the IV is discontinued. The HR and BP are also typically monitored for 15-30 minutes after completion of the IV administration.

In another aspect, the present invention provides a novel pharmaceutical composition, comprising: a syringe, comprising: from 60-125 mg of sotalol. In another example, the syringe consists essentially of 60-125 mg of sotalol and at least one diluent selected from: saline, 5% dextrose in water (D5W), and Ringer's lactate.

In another aspect, the syringe, comprises: 60 mg of sotalol. In another example, the syringe consists essentially of 60 mg of sotalol and at least one diluent selected from: saline, 5% dextrose in water (D5W), and Ringer's lactate.

In another aspect, the syringe, comprises: 75 mg of sotalol. In another example, the syringe consists essentially of 75 mg of sotalol and at least one diluent selected from: saline, 5% dextrose in water (D5W), and Ringer's lactate.

In another aspect, the syringe, comprises: 82.5 mg of sotalol. In another example, the syringe consists essentially of 82.5 mg of sotalol and at least one diluent selected from: saline, 5% dextrose in water (D5W), and Ringer's lactate.

In another aspect, the syringe, comprises: 90 mg of sotalol. In another example, the syringe consists essentially of 90 mg of sotalol and at least one diluent selected from: saline, 5% dextrose in water (D5W), and Ringer's lactate.

In another aspect, the syringe, comprises: 105 mg of sotalol. In another example, the syringe consists essentially of 105 mg of sotalol and at least one diluent selected from: saline, 5% dextrose in water (D5W), and Ringer's lactate.

In another aspect, the syringe, comprises: 112.5 mg of sotalol. In another example, the syringe consists essentially of 112.5 mg of sotalol and at least one diluent selected from: saline, 5% dextrose in water (D5W), and Ringer's lactate.

In another aspect, the syringe, comprises: 125 mg of sotalol. In another example, the syringe consists essentially of 125 mg of sotalol and at least one diluent selected from: saline, 5% dextrose in water (D5W), and Ringer's lactate.

In another aspect, the volume of liquid in the syringe is from 5, 6, 7, 8, 9, to 10 mL.

In another aspect, the syringe is filled from a vial of 15 mg/mL of sotalol and further diluted to a final volume of 10 mL, wherein the diluent is selected from saline, 5% dextrose in water (D5W), and Ringer's lactate.

The present invention may be embodied in other specific forms without departing from the spirit or essential attributes thereof. This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Other features of the invention will become apparent in the course of the following descriptions of exemplary embodiments that are given for illustration of the invention and are not intended to be limiting thereof.

EXAMPLES

Example Sotalol Protocol

Infuse the loading dose over one hour.

Monitor QTc interval every 15 minutes during infusion.

Continue to monitor QTc around Tmax (2 to 4 hours post-dose) following the first oral dose (in all patients) and second oral dose (in patients with CrCl≥60 mL/min).

If the QTc interval prolongs to >500 ms or increases 20% from baseline when initiating for an oral dose of 80 mg, discontinue drug; if initiating for an oral dose of 120 mg discontinue drug and consider a lower dose. If re-initiation at a lower dose of 80 mg is desired, wait at least 1 day (in patients with CrCl≥60 mL/min), or at least 3 days (in patients with CrCl≥30 to <60 mL/min), or 7 days (in patients with CrCl≥10 to <30 mL/min).

Numerous modifications and variations of the present invention are possible considering the above teachings. It is therefore to be understood that within the scope of the appended claims, the invention may be practiced otherwise than as specifically described herein.

The invention claimed is:

1. A method of administering sotalol hydrochloride, comprising:
   a. administering an intravenous (IV) dose of 125-135 mg sotalol hydrochloride over a period of 1 hour to a subject having had symptomatic atrial fibrillation or atrial flutter, wherein the subject is currently in sinus rhythm; and
   b. after completion of the IV dose, administering oral dosing of one or more oral dose of sotalol hydrochloride to the subject in an amount of 120 mg.

2. The method of claim 1, wherein the oral dosing is initiated 4-12 hours after completion of the IV dose.

3. The method of claim 1, wherein one or more of the oral doses are administered at a 12-48 hour interval from initiation of the oral dosing.

4. The method of claim 3, wherein:
   the oral dosing is initiated 4-6 hours after completion of the IV dose; and
   one or more of the oral doses are administered at a 12-24 hour interval from initiation of the oral dosing.

5. The method of claim 3, wherein the oral dosing is initiated 4-12 hours after completion of the IV dose.

6. The method of claim 2, wherein:
   the oral dosing is initiated 4-6 hours after completion of the IV dose; and
   one or more of the oral doses are administered at a 12-48 hour interval from initiation of the oral dosing.

7. The method of claim 6, wherein:
   one or more of the oral doses are administered at a 12 hour interval from initiation of the oral dosing.

* * * * *